US00PP25668P2

(12) United States Plant Patent
Danziger

(10) Patent No.: US PP25,668 P2
(45) Date of Patent: Jun. 30, 2015

(54) ***BIDENS* PLANT NAMED 'DANBID7346'**

(50) Latin Name: *Bidens ferulifolia*
Varietal Denomination: DANBID7346

(71) Applicant: Danziger—"Dan" Flower Farm, Moshav Mishmar Hashiva (IL)

(72) Inventor: Gavriel Danziger, Moshav Nir-Zvi (IL)

(73) Assignee: Danziger—"Dan" Flower Farm, Moshav Mishmar Hashiva (IL)

( * ) Notice: Subject to any disclaimer, the term of this patent is extended or adjusted under 35 U.S.C. 154(b) by 140 days.

(21) Appl. No.: 13/987,947

(22) Filed: Sep. 18, 2013

(51) Int. Cl.
*A01H 5/02* (2006.01)

(52) U.S. Cl.
USPC ..... Plt./410

(58) Field of Classification Search
USPC ..... Plt./410
See application file for complete search history.

*Primary Examiner* — Susan McCormick Ewoldt
(74) *Attorney, Agent, or Firm* — Audrey Charles

(57) ABSTRACT

A new and distinct cultivar of *Bidens* plant named 'DANBID7346', characterized by its medium yellow-colored inflorescences, dark green-colored foliage, and moderately vigorous, compact-mounded growth habit, is disclosed.

1 Drawing Sheet

Latin name of genus and species of plant claimed: *Bidens ferulifolia.*

Variety denomination: 'DANBID7346'.

BACKGROUND OF THE INVENTION

The present invention relates to a new and distinct cultivar of *Bidens* plant botanically known as *Bidens ferulifolia* and hereinafter referred to by the cultivar name 'DANBID7346'.

The new cultivar originated in a controlled breeding program in Moshav Mishmar Hashiva, Israel during October 2006. The objective of the breeding program was the development of *Bidens* cultivars with a densely branched, compact-mounded growth habit.

The new *Bidens* cultivar is the result of open-pollination. The female (seed) parent of the new cultivar is the proprietary *Bidens ferulifolia* breeding selection coded BD-6-244, not patented, characterized by its medium yellow-colored flowers, medium green-colored foliage, low growth vigor and prostrate growth habit. The male (pollen) parent of the new cultivar is unknown. The new cultivar was discovered and selected as a single flowering plant within the progeny of the above stated open-pollination during May 2007 in a controlled environment in Moshav Mishmar Hashiva, Israel.

Asexual reproduction of the new cultivar by terminal stem cuttings since May 2007 in Moshav Mishmar Hashiva, Israel and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'DANBID7346' as a new and distinct cultivar of *Bidens* plant:

1. Medium yellow-colored inflorescences;
2. Dark green-colored foliage; and
3. Moderately vigorous, compact-mounded growth habit.

Plants of the new cultivar differ from plants of the female parent primarily in having larger-sized flowers and a mounded growth habit.

Of the many commercially available *Bidens* cultivars, the most similar in comparison to the new cultivar is the parent cultivar Bidy Gonzales Big 'Duebigonbi', U.S. Plant Pat. No. 23,682. However, in comparison, plants of the new cultivar differ from plants of 'Duebigonbi' in at least the following characteristics:

1. Plants of the new cultivar are taller than plants of 'Duebigonbi'; and
2. Plants of the new cultivar have lighter colored ray florets than plants of 'Duebigonbi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'DANBID7346'. The plants were grown in 4.5-inch pots for 8 weeks in a greenhouse in West Chicago, Ill.

DETAILED BOTANICAL DESCRIPTION

Figure 1:
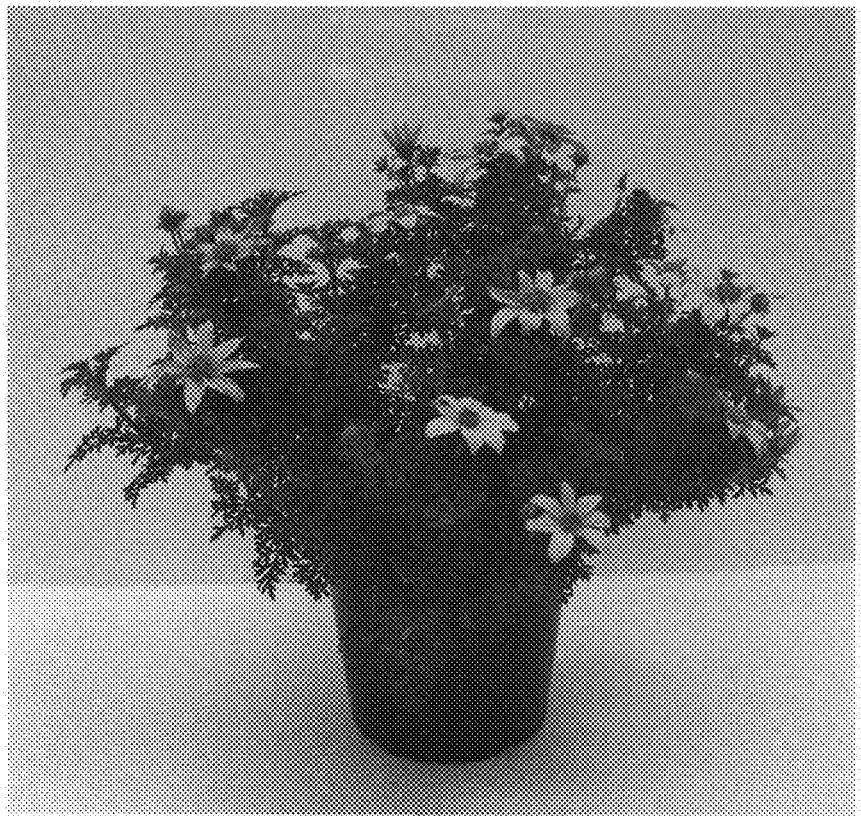
FIG. 1 illustrates a side view of the overall growth and flowering habit of 'DANBID7346'.
Figure 2:
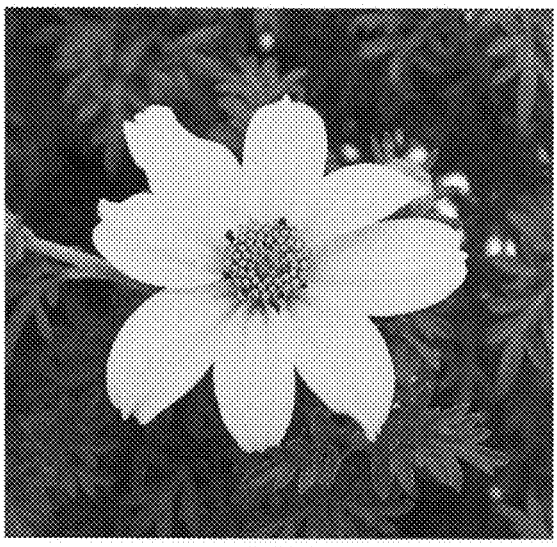
FIG. 2 illustrates a close-up view of an individual inflorescence of 'DANBID7346'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2013 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 8 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Bidens ferulifolia* cultivar DANBID7346.

Parentage:

*Female parent.*—Proprietary *Bidens ferulifolia* breeding selection coded BD-6-244, not patented.

*Male parent.*—Unknown.

Propagation:

*Type cutting.*—Terminal stem.

*Time to initiate roots.*—Approximately 6 to 9 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, compact-mounded growth habit.

*Size.*—Height from soil level to top of plant plane: Approximately 14.5 cm. Width: Approximately 23.5 cm.

*Branching habit.*—Freely branching, pinching enhances basal branching. Quantity of main branches per plant: Approximately 6.

*Branch.*—Strength: Strong. Length: Approximately 13.0 cm. Diameter: Approximately 3.0 mm. Length of central internode: Approximately 7.0 mm. Texture: Densely pubescent. Color of young stem: 147D. Color of mature stem: 147D with an overlay of 187B.

Foliage description:

*General description.*—Quantity of leaves per main branch: Approximately 18. Fragrance: None. Form: Simple. Arrangement: Opposite, decussate.

*Leaves.*—Aspect: Petiole is at an acute angle to stem, blade is perpendicular to stem. Shape: Ovate. Margin: Deeply bipinnatifid. Apex of divisions: Acuminate. Base of divisions: Attenuate. Venation pattern: Pinnate. Length of mature leaf: Approximately 2.3 cm. Width of mature leaf: 2.1 cm. Texture of upper and lower surfaces: Sparsely pubescent. Color of upper surface of young foliage: 137A with indistinguishable venation. Color of lower surface of young and mature foliage: 138B with indistinguishable venation. Color of upper surface of mature foliage: N137A with indistinguishable venation.

*Petiole.*—Length: Approximately 5.0 mm. Diameter: Approximately 2.0 mm. Texture: Densely pubescent. Color: 147D.

Flowering description:

*Flowering habit.*—'DANBID7346' is freely flowering under outdoor growing conditions with substantially continuous blooming from spring through autumn and year-round in greenhouse environment.

*Lastingness of individual inflorescence on the plant.*—Approximately 9 to 11 days.

Inflorescence description:

*General description.*—Type: Daisy-type composite, actinomorphic. Persistent. Shape: Round. Aspect: Facing upright. Arrangement: Above the foliage. Quantity per plant: Approximately 16. Diameter: Approximately 3.8 cm. Depth: Approximately 8.0 mm. Fragrance: Mild.

*Peduncle.*—Strength: Strong. Aspect: Erect, arising from leaf axils. Length: Approximately 2.7 cm. Diameter: Approximately 1.0 mm. Texture: Densely pubescent. Color: 145A.

*Bud.*—Rate of opening: Generally takes 4 to 5 days for bud to progress from first color to fully open flower. Quantity per plant: Approximately 15.

*Bud just before opening.*—Shape: Ovoid. Diameter: Approximately 7.0 mm. Color: 1B.

*Ray florets.*—Quantity per inflorescence: Approximately 7 to 8. Arrangement: Imbricate in a single whorl. Aspect: Slightly concave. Shape: Ovate. Margin: Entire. Apex: Three acute tips. Base: Obtuse. Length: Approximately 2.1 cm. Width: Approximately 1.0 cm. Texture of upper surface: Glabrous. Texture of lower surface: Glabrous, ribbed. Color of upper surface when first and fully open: 12A. Color of lower surface when first and fully open: 12B.

*Disc florets.*—Quantity per inflorescence: Approximately 65. Arrangement: Massed in center of inflorescence. Shape: Tubular. Margin: Entire. Apex: Five acute tips. Base: Fused. Length: Approximately 7.0 mm. Diameter at apex: Approximately 1.0 mm. Diameter at base: Approximately 1.0 mm. Texture: Glabrous. Color when first and fully open: 14B, translucent.

*Disc.*—Diameter: Approximately 8.0 mm. Depth: Approximately 6.0 mm.

*Receptacle.*—Shape: Concave. Height: Approximately 2.0 mm. Diameter at base: Approximately 4.0 mm. Color: 145D.

*Phyllaries.*—Quantity per inflorescence Approximately 16. Arrangement: In two whorls. Shape: Linear to lanceolate. Margin: Entire. Apex: Acute. Base: Entire. Length: Approximately 6.0 mm. Width: Approximately 1.0 to 2.0 mm. Texture of upper and lower surfaces: Moderately pubescent. Color of upper surface: 137A. Color of lower surface: 137B.

*Reproductive organs.*—Androecium: Present on disc florets only. Stamen quantity: 5 per floret. Stamen length: Approximately 5.0 mm. Anther shape: Linear. Anther length: Approximately 2.0 mm. Anther color: 200A. Pollen amount: Moderate. Pollen color: 16A. Gynoecium: Present on ray and disc florets. Pistil quantity: 1 per floret. Pistil length: Approximately 7.0 mm. Stigma shape: Bifurcate. Stigma length: Approximately 1.0 mm. Stigma color: Closest to 15A. Style length: Approximately 5.0 mm. Style color: 154D, translucent. Ovary length: Approximately 1.0 mm. Ovary color: 145D.

Seed and fruit production: Neither seed nor fruit production has been observed.

Disease and pest resistance: Resistance to pathogens and pests common to *Bidens* has not been observed.

What is claimed is:

1. A new and distinct cultivar of *Bidens* plant named 'DANBID7346', substantially as herein shown and described.

* * * * *